United States Patent [19]

Yang

[11] Patent Number: 4,981,033

[45] Date of Patent: Jan. 1, 1991

[54] GAGE FOR ROCKET MOTOR DATA ACQUISITION

[76] Inventor: Lien C. Yang, 2107 Normanton Dr., LaCanada, Calif. 91011

[21] Appl. No.: 519,045

[22] Filed: May 4, 1990

[51] Int. Cl.⁵ ............................................. G01M 15/00
[52] U.S. Cl. ........................................ 73/116; 324/459
[58] Field of Search .................. 73/116; 324/464, 459, 324/71.2

[56] References Cited

U.S. PATENT DOCUMENTS

| | | | |
|---|---|---|---|
| 3,090,197 | 5/1963 | Lapp et al. | 60/35.6 |
| 3,701,278 | 10/1972 | Askins et al. | 73/35 |
| 3,946,607 | 3/1976 | Panella | 73/167 |
| 4,584,531 | 4/1986 | Couch | 324/464 |

Primary Examiner—Jerry W. Myracle
Attorney, Agent, or Firm—Kenneth L. Warsh; Robert M. Wohlfarth

[57] ABSTRACT

A device of monitoring propellant burning within, and erosion of, a rocket motor case by measuring the voltage-induced capacity of gages on the external surface of the case is described. A burning propellant generates a conducting gas within the burn front inside the motor. The resultant voltage is caused by an injected voltage pulse on a metal igniter ring in contact with or capacitively coupled to the gas.

4 Claims, 1 Drawing Sheet

U.S. Patent  Jan. 1, 1991  4,981,033
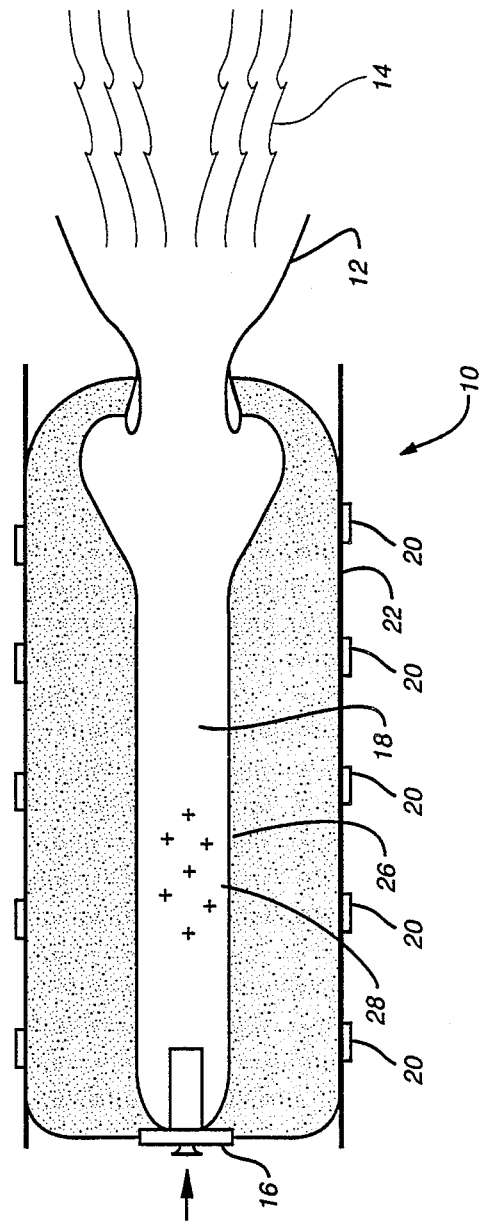
FIG._1
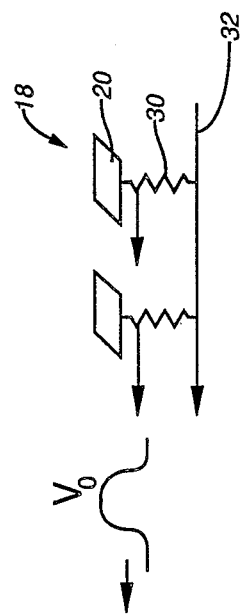
FIG._2

GAGE FOR ROCKET MOTOR DATA ACQUISITION

FIELD OF THE INVENTION

This invention pertains to a method and apparatus for rocket motor data acquisition and more particularly to a means for monitoring internal rocket motor conditions.

BACKGROUND OF THE INVENTION

When testing a new solid rocket motor design it is desirable to know distribution and rates of burning within different regions of the fuel, so that the fuel can be best shaped to obtain a full burn.

Monitoring of internal rocket motor conditions during a test burn has been a difficult problem. Probes which penetrate the pressure vessel can cause vessel failure. Furthermore, most probes cannot withstand the high temperature conditions within the burning rocket.

Capacitance and magnetic gages have been used for many years with conducting gases in shock-tube laboratory technology. This invention is an extension of laboratory techniques to the interior of a burning rocket.

OBJECTIVES OF THE INVENTION

It is therefore a primary objective of the present invention to provide a means for monitoring the combustion front proximity, local propellant and insulation erosion rates and abnormal patterns inside a rocket motor, both in flight and on the ground.

SUMMARY OF THE INVENTION

These objects of the invention and other objects, features and advantages to become apparent as the specification progresses are accomplished by the invention according to which, briefly stated, the burning rocket propellant generates a conducting gas which forms within the burn front inside the rocket motor. A resultant voltage signal is generated by an injected voltage pulse on a metal igniter ring in contact with the gas, or capacitively coupled to the gas via the propellant.

Other objects, advantages and novel features of the present invention will be apparent from the following detailed description when read in light of the accompanying drawing and claims.

LIST OF ADVANTAGES OF THE INVENTION

An important advantage of the present invention is that burn of a solid rocket fuel can be mapped as a function of time without invading the combustion chamber or penetrating the motor casing.

These and further objectives, constructional and operational characteristics, and advantages of the invention will no doubt be more evident to those skilled in the art from the detailed description given hereinafter with reference to the figures of the accompanying drawings which illustrate a preferred embodiment by way of non-limiting example.

BRIEF DESCRIPTION OF THE DRAWINGS

FIG. 1 shows a schematic representation of a solid propellant rocket motor cross section.

FIG. 2 is a schematic representation of the plasma capacitance gage circuitry.

GLOSSARY

The following is a glossary of elements and structural members as referenced and employed in the present invention.

10 rocket motor
12 nozzle
14 combustion products
16 igniter
18 motor cavity
20 detectors
22 motor case
24 propellant
26 combustion contours
28 ionized gas
30 resistors
32 ground wire

DESCRIPTION OF THE PREFERRED EMBODIMENTS

There has been an ongoing need to develop a miniature real-time instrumentation system capable of monitoring the combustion front proximity, local propellant and insulation erosion rates and abnormal burning patterns inside a rocket motor. This led to the development of the present invention, a plasma capacitance gage capable of providing information to facilitate motor performance prediction, failure analysis, design and design corrections. Further, this gage is useful in diagnosing propellant uniformity, interface integrity, stress and pressure on the motor and electrical properties of the exhaust gas plume.

Referring now to the drawings wherein like reference numerals are used to designate like or corresponding parts throughout the various figures thereof, there is shown in FIG. 1 a schematic representation of a rocket motor 10 in conjunction with the plasma capacitance gage system. The rocket motor has a nozzle 12 through which the combustion products 14 exit the motor 10. At the end of the rocket opposite to motor 10 there is an igniter 16. This system measures the capacitance between the flame in the motor cavity 18 and a plurality of detectors 20 attached to the motor case 22. The capacitance increases as the propellant 24 or insulation erodes away. The motor cavity 18 boundary is defined by the combustion contour 26. As the propellant 18 burns, the distance between the burn front contour 26 and the detectors 20 decreases, thereby increasing the capacitance.

The main advantage of this approach is that it requires no perturbation inside the motor case. Additionally, placement of the detectors 20 on the motor case 22 does not introduce large aerodynamic drag forces. A further advantage is that the plasma capacitance gage system requires a minimal number signal channels for transmission during flight.

During operation, the combustion flame in the motor cavity 18 has a high temperature, in the order of 2000–3000° K., thereby rendering the gaseous product electrically conductive.

This concept is illustrated by the figure which depicts a solid rocket propellant motor 10 in operation. Because the combustion flame in the motor cavity 12 has a high temperature in the order of 2000–3000° K., ionization will occur in the gaseous product, i.e. the latter is electrically conductive. It is therefore possible to impose a transient voltage of adequate amplitude onto this ionized gas 28 inside the burning cavity 18. On the exterior surface of the non-metallic motor case flat metal foil electrodes are attached at selected locations to form the detectors 20. A transient voltage is imposed on the ionized gas 28 through the igniter 16.

Resistors 30 which function as current shunts can also be made in thin chip form to be easily attached to the motor case surface between the detectors 20 and ground wire 32. Electrical wires can be either thin twisted pairs or flat transmission lines. The entire system cam be attached to the motor case exterior surface without significant impact on the aerodynamic characteristics of the case surface. For further protection a thin layer of epoxy can be applied over these components.

This invention is not limited to the preferred embodiment and alternatives heretofore described, to which variations and improvements may be made, without departing from the scope of protection of the present patent and true spirit of the invention, the characteristics of which are summarized in the following claims.

What is claimed is:

1. A method of mapping the burning of a solid rocket fuel as a function of time in a rocket having a non-metallic case comprising the steps of:
    (a) attaching a multiplicity of metal electrodes to the outside of the rocket case at points distributed over the length of the case
    (b) inducing voltage pulses of known voltage on the combustion gases, and
    (c) measuring resultant voltage pulses at the electrodes.

2. The method of claim 1 wherein said step of inducing voltage pulses of known voltage on the combustion gases is performed by imposing said voltage pulses at the exterior of said case on a metallic igniter part which provides a conduction path into said combustion gases.

3. The method of claim 1 wherein said step of inducing voltage pulses of known voltage on the combustion gases is performed by capacitatively coupling said voltages through an igniter.

4. Apparatus for mapping the burn of a solid rocket propellant within a non-metallic rocket case comprising:
    (a) a multiplicity of metallic foils attached to the outside of the rocket case
    (b) means for imposing a voltage pulse on ionized combustion gases within the rocket and
    (c) means for measuring the amplitude of a resultant voltage pulse at said foils.

* * * * *